US00RE42843E

(19) United States
(12) Reissued Patent
Strickland et al.

(10) Patent Number: US RE42,843 E
(45) Date of Reissued Patent: Oct. 18, 2011

(54) NASAL CANNULA

(75) Inventors: Roger Strickland, Blackshear, GA (US); Jonathan Lee, St. Augustine, FL (US); Thomas J. Wood, Coconut Creek, FL (US)

(73) Assignee: Innomed Technologies, Inc., Coconut Creek, FL (US)

( * ) Notice: This patent is subject to a terminal disclaimer.

(21) Appl. No.: 11/334,822

(22) Filed: Jan. 19, 2006
(Under 37 CFR 1.47)

Related U.S. Patent Documents

Reissue of:
(64) Patent No.: 6,679,265
Issued: Jan. 20, 2004
Appl. No.: 10/042,042
PCT Filed: Oct. 25, 2001

(51) Int. Cl.
*A61M 15/08* (2006.01)
*A62B 18/02* (2006.01)
*A62B 7/00* (2006.01)
*A62B 18/08* (2006.01)

(52) U.S. Cl. ..... 128/207.18; 128/207.11; 128/207.13

(58) Field of Classification Search ..... 128/200.24, 128/202.18, 203.22, 203.29, 204.12, 205.25, 128/206.11, 206.12, 206.18, 206.27, 206.28, 128/207.11, 207.13, 207.14, 207.18; 600/529, 600/532, 538
See application file for complete search history.

(56) References Cited

U.S. PATENT DOCUMENTS

| | | | | | |
|---|---|---|---|---|---|
| 1,362,766 | A | * | 12/1920 | McGargill | 128/205.27 |
| 2,663,297 | A | * | 12/1953 | Turnberg | 128/207.13 |
| 4,156,426 | A | * | 5/1979 | Gold | 128/204.18 |
| 4,367,735 | A | * | 1/1983 | Dali | 128/207.18 |
| 4,422,456 | A | * | 12/1983 | Tiep | 128/207.18 |
| 4,915,105 | A | * | 4/1990 | Lee | 128/205.27 |
| 4,919,128 | A | * | 4/1990 | Kopala et al. | 128/207.18 |
| 4,996,983 | A | * | 3/1991 | AmRhein | 128/206.11 |
| 5,046,491 | A | * | 9/1991 | Derrick | 128/200.24 |
| 5,137,017 | A | * | 8/1992 | Salter | 128/207.18 |
| 5,165,133 | A | * | 11/1992 | Armbruster | 15/97.1 |
| 5,269,296 | A | | 12/1993 | Landis | |
| 5,335,659 | A | * | 8/1994 | Pologe | 600/473 |
| 5,400,776 | A | * | 3/1995 | Bartholomew | 128/200.24 |
| 5,477,852 | A | * | 12/1995 | Landis et al. | 128/207.18 |
| 5,513,634 | A | * | 5/1996 | Jackson | 128/207.18 |
| 5,533,506 | A | | 7/1996 | Wood | |
| 5,682,881 | A | * | 11/1997 | Winthrop et al. | 128/207.18 |
| 5,687,715 | A | | 11/1997 | Landis et al. | |
| 5,724,965 | A | | 3/1998 | Handke et al. | |
| 5,794,619 | A | * | 8/1998 | Edelman et al. | 128/207.18 |
| 5,928,189 | A | * | 7/1999 | Phillips et al. | 604/65 |

(Continued)

OTHER PUBLICATIONS

U.S. Appl. No. 12/842,271, filed Jul. 23, 2010, for Nasal Cannula.

*Primary Examiner* — Justine Yu
*Assistant Examiner* — Kristen C Matter
(74) *Attorney, Agent, or Firm* — Bacon & Thomas, PLLC

(57) ABSTRACT

A nasal cannula for delivering air to a patient's nares. Two delivery tubes are provided to supply air to a pair of nasal inserts each of which conform to the shape of the nare. Properly placed bleed ports reduce noise and reduce carbon dioxide retained in the system. The cannula is positioned on the face with the aid of a strap system.

15 Claims, 5 Drawing Sheets

U.S. PATENT DOCUMENTS

| | | | | |
|---|---|---|---|---|
| 6,165,133 | A | 12/2000 | Rapoport et al. | |
| 6,213,955 | B1 * | 4/2001 | Karakasoglu et al. | 600/529 |
| 6,298,850 | B1 * | 10/2001 | Argraves | 128/207.17 |
| 6,354,293 | B1 * | 3/2002 | Madison | 128/204.13 |
| 6,422,240 | B1 * | 7/2002 | Levitsky et al. | 128/207.18 |
| 6,439,234 | B1 * | 8/2002 | Curti et al. | 128/207.18 |
| 6,478,026 | B1 * | 11/2002 | Wood | 128/207.18 |
| 6,478,029 | B1 * | 11/2002 | Boyd et al. | 128/898 |
| 6,595,215 | B2 * | 7/2003 | Wood | 128/207.18 |
| 6,679,265 | B2 | 1/2004 | Strickland et al. | |
| 6,776,162 | B2 | 8/2004 | Wood | |
| 6,807,967 | B2 * | 10/2004 | Wood | 128/207.18 |
| 6,863,069 | B2 * | 3/2005 | Wood | 128/207.18 |
| 6,994,089 | B2 | 2/2006 | Wood | |
| 6,997,177 | B2 | 2/2006 | Wood | |
| 6,997,187 | B2 | 2/2006 | Wood et al. | |
| 7,000,613 | B2 | 2/2006 | Wood et al. | |
| 7,047,974 | B2 * | 5/2006 | Strickland et al. | 128/207.18 |
| 7,059,328 | B2 * | 6/2006 | Wood | 128/207.18 |
| 7,188,624 | B2 * | 3/2007 | Wood | 128/207.18 |
| 7,191,781 | B2 | 3/2007 | Wood | |
| 7,234,465 | B2 | 6/2007 | Wood | |
| 2002/0059935 | A1 * | 5/2002 | Wood | 128/207.18 |
| 2002/0162558 | A1 * | 11/2002 | Noble | 128/207.18 |
| 2004/0182397 | A1 | 9/2004 | Wood | |
| 2005/0028821 | A1 | 2/2005 | Wood et al. | |
| 2005/0039757 | A1 | 2/2005 | Wood | |
| 2005/0121037 | A1 | 6/2005 | Wood | |
| 2005/0133040 | A1 | 6/2005 | Wood | |
| 2005/0235999 | A1 | 10/2005 | Wood et al. | |
| 2005/0252515 | A1 | 11/2005 | Wood | |
| 2007/0137653 | A1 | 6/2007 | Wood | |

* cited by examiner

NASAL CANNULA

Matter enclosed in heavy brackets [ ] appears in the original patent but forms no part of this reissue specification; matter printed in italics indicates the additions made by reissue.

FIELD OF THE INVENTION

The present invention relates generally to a nasal mask or cannula and more particularly to a nasal cannula for treating a patient with a positive ventilation pressure machine for assisted ventilation.

BACKGROUND OF THE INVENTION

Positive air pressure (PAP) assisted ventilation systems have been adopted for the treatment of various disorders. PAP systems are commonly used to treatment sleep apnea. Variations of PAP systems have been used to administer drugs and the like.

In operation the patient's respiration is assisted by an external pump which supplies air to the patient under a slight positive pressure. In the conventional system, air is delivered in response to preset conditions selected for each individual patient. In normal operation the patient's inspiratory phase is assisted by a pump which delivers an adequate supply of air at a slight positive pressure to a mask or cannula that is placed on the face of the patient. Full face mask systems which cover both the mouth and the nose are used. Systems which cover the mouth or nose alone are also common.

In use, when the patient exhales, the higher pressure in the mask or cannula system is used to open an exhaust valve. Thus the patient respiration is assisted on the inhalation phase by positive pressure while the expiration phase takes place at approximately atmospheric pressure.

In instances where the patient compliance is affected by the comfort of the mask it is now widely accepted that "nose only" cannula devices are preferred. Examples of current devices can be seen in U.S. Pat. No. 5,477,852 to Landis; U.S. Pat. No. 5,533,506 to Wood; U.S. Pat. No. 5,269,296 to Landis; U.S. Pat. No. 5,687,715 to Landis; U.S. Pat. No. 5,724,965 to Handke.

SUMMARY OF THE INVENTION

In contrast to prior air nasal masks, the present system includes a pair of nasal inserts which are fed bilaterally from a pair of delivery tubes which includes both a left and a right leg. If the patient occludes one leg on one side of the mask, the complimentary side is sufficient to provide all of the air required by the patient.

Air is introduced into the system through a Y-shaped adapter or coupler. The shape of the coupler cooperates with other elements to minimize noise.

A pair of bleed ports are placed in the cannula body near the patient's nose. These bleed ports reduce the amount of carbon dioxide retained by the system. The two complex ports are placed in the cannula body to reduce noise and to reduce carbon dioxide build up in the system. Example calculations show how the size, shape and location of each of these ports cooperate to reduce the inhaled carbon dioxide concentration.

An additional feature relates directly to the shape of the nasal inserts. The nasal inserts are sufficiently long and compliant that they may be inserted into the nose until they adopt a location where the cross-section of the nare and the cross-section of the insert are essentially equal. The compliance of the material used to manufacturer the device is sufficient to provide an extremely comfortable fit in the nares.

BRIEF DESCRIPTION OF THE DRAWING

Throughout the figures of the drawing like reference numerals indicate identical structure wherein.

DETAILED DESCRIPTION

Figure 1:
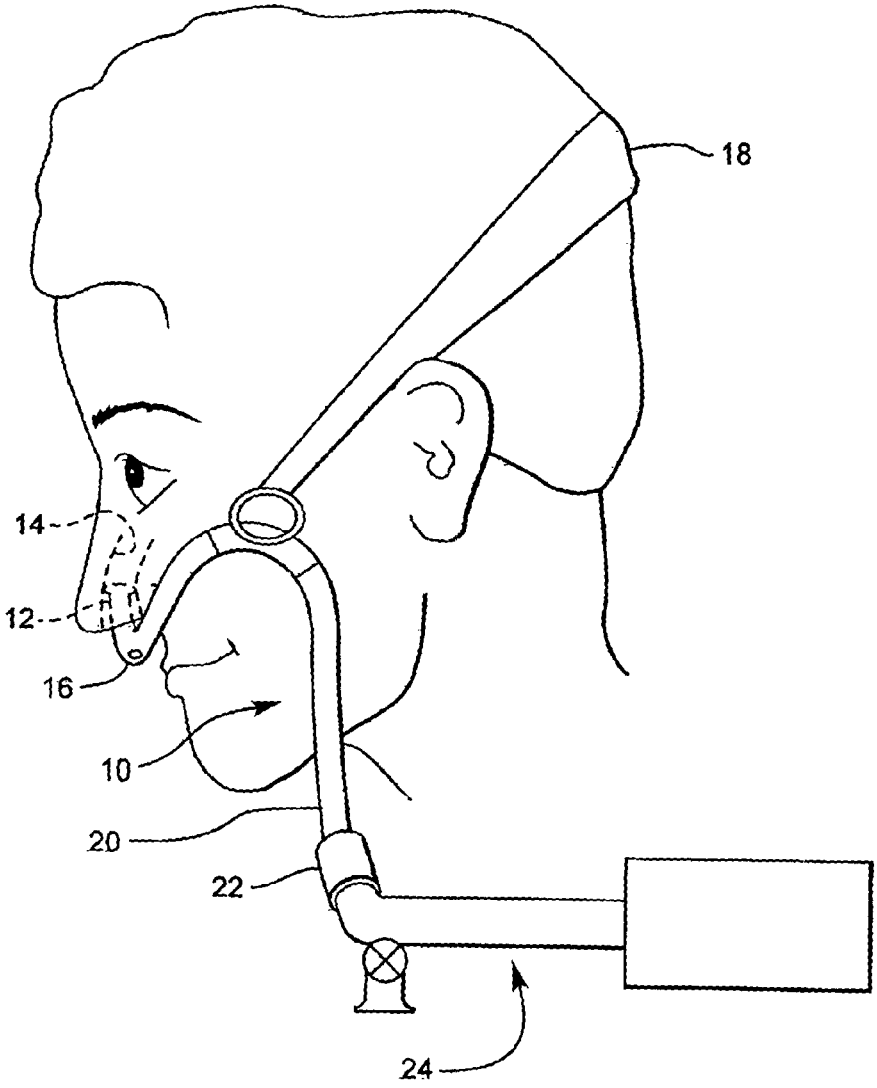
FIG. 1 is a schematic representation of the nasal cannula on the head of a user.

Turning to FIG. 1 there is shown a nasal cannula 10 which shows a nasal insert 12 placed into a patient's nare 14. Directly beneath each nasal insert is a bleed port as seen at reference numeral 16. The complete nasal cannula is held on the patient's face with a strap system 18 which may be of any convenient and conventional construction. The left and right delivery tubes typified by delivery tube 20 terminate in a coupler 22. This Y-shaped coupler 22 is connected to a conventional positive pressure ventilation machine 24.

In operation, the positive pressure ventilation machine 24 supplies air under pressure to the nasal cannula 10 and releases exhaled air to the atmosphere. Conventional machines have a valve that is overpressure during exhalation to exhaust air. In some instances the system may also warm and humidify the delivered air. In some instances the machines are used to deliver medications.

The left delivery tube and the right delivery tube 20 should lie close to the face of the patient and the coupler 22 should be positioned in the vicinity of the neck as seen in the figure.

Figure 2:
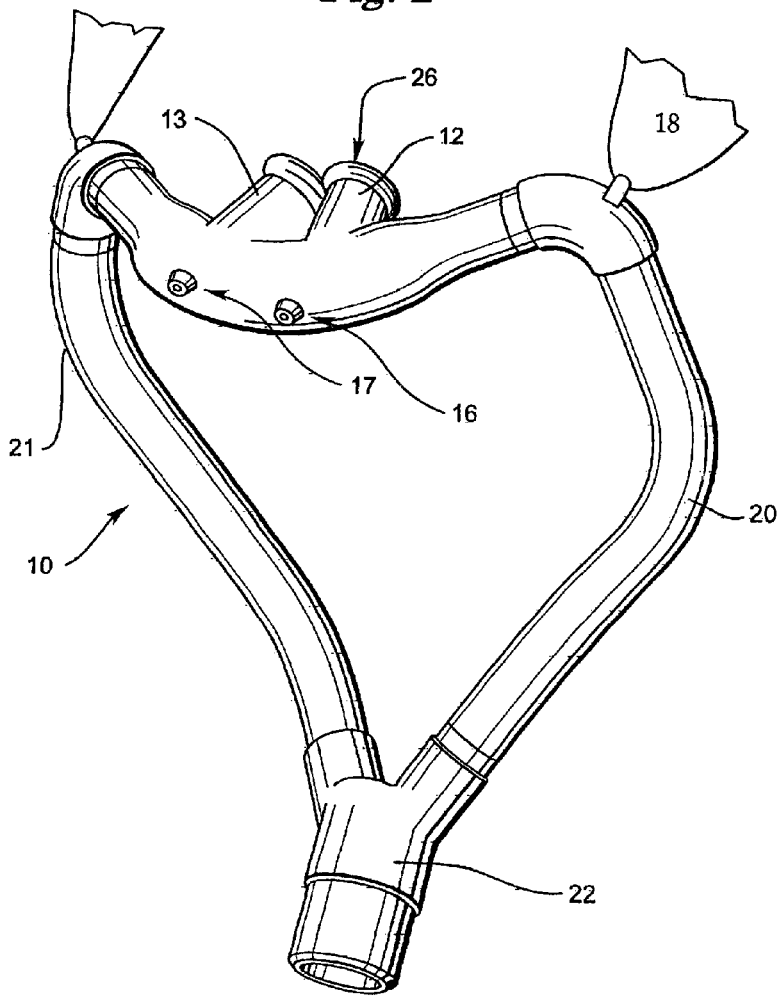
FIG. 2 is a projection of the nasal cannula in isolation.

FIG. 2 shows the nasal cannula 10 in perspective view. The entire cannula 10 may be molded out of a polymeric material such as silicone rubber or urethane. Portions of the nasal cannula may be locally reinforced to increase rigidity. For example it may be useful to reinforce the structure at the location where the strap 18 system meets the cannula device 10 In the figure a portion of the strap system 18 is shown coupled to delivery tube 20. The various changes in section depicted in the figure add stiffness or rigidity to the device. The optimal shape and cross section is not known and some experimentation may be required to optimize the device. However the softness and compliance of the elastomer is an important factor in patient comfort. The Y-shaped connector 22 is adapted for connection to the PAP system 24.

Nasal insert 12 and nasal insert 13 are tubes connected to and extending from the delivery tube 20 and delivery tube 21 respectively. The most distal portion of the insert 12 terminates in a flange 26. It is expected that each flange 26 will be quite soft. The flange 26 is designed to readily conform to the patient's nare. In use the patient will direct the inserts into the nose and the inserts 12 and 13 will move in the nare until the *inner* cross section of the nare matches the *outer* cross section of the flange. The anatomy of the nose will deform the shape of the insert and its flange to achieve a comfortable seal. It is expected that only one or two sizes will be required to fit a large population as most patients have similarly sized nares.

The bleed port typified by port 16 is a tube extending from the delivery tube 20 into the insert 12. Each tube has a characteristic height or length. These bleed ports serve several functions. If the bleed ports 16 and 17 are appropriately placed and sized they can reduce the accumulation of carbon dioxide. If they are properly configured, sized and located they can also be used to decrease "whistling" or other acoustic effects. One objective of the bleed ports is to decreases the amount of carbon dioxide in the cannula during inhalation to a targeted value between 0.2 to 0.7 percent. A preferred value is below approximately 0.5 percent. Applicant believes that low carbon dioxide concentrations in the system will prevent build up of carbon dioxide in the patient.

Figure 3:
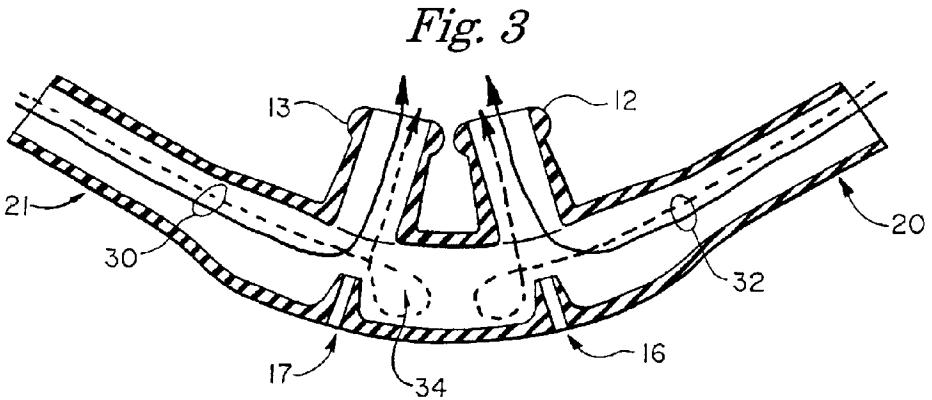
FIG. 3 is cross section of a portion of the nasal cannula showing the bleed ports.

FIG. 3 is a composite and schematic view that shows the air flow in the nasal cannula 10 during normal inhalation. Inspired air seen as arrows 30 and 32 depict flow under pressure from the air source 24. A small flow depicted by vortex 34 enters the space between insert 12 and insert 13. In normal operation each side of the system carries one half of the required flow.

Figure 4:
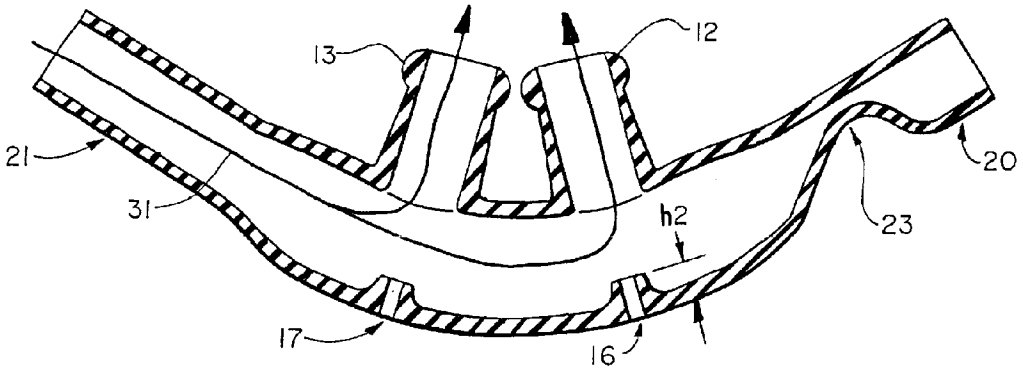
FIG. 4 is cross section of a portion of the nasal cannula showing the bleed ports.

FIG. 4 is a composite and schematic view that depicts an occlusion 23 or pinch off in the delivery tube 20. In use, when one of the delivery tubes such as delivery tube 20 is closed off by patient movement or the like, there is still sufficient air supplied through the alternate delivery tube 21 as indicated by the airflow 31 depicted in the figure. In this instance the full amount of air enters the patient through inserts 12 and 13 of the system. In the figure the height or length of the bleed port is shown as "h2" and this represents a minimum height bleed port 16. It is expected that the minimum height is twice the delivery tube thickness at the location of the bleed port.

Figure 5:
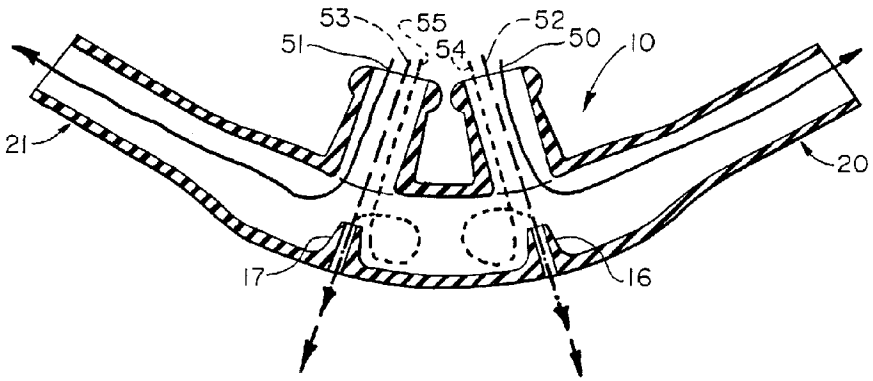
FIG. 5 is cross section of a portion of the nasal cannula showing the bleed ports.

FIG. 5 is a composite and schematic view that shows the idealized airflow in the nasal cannula 10. There are three distinct exit paths. Path 50 and path 51 depict flow back to the exhaust valve of the ventilator 24. This flow overpowers the exhaust valve and most of this flow leaves the system. Path 52 and 53 show exhaust directly through the bleed ports 16 and 17 respectively. The paths identified by path arrows 54 and 55 reflect complex scavenging of the volume between the inserts. This flow dilutes the air in the volume and helps to reduce carbon dioxide.

Throughout the figures and specification the following definitions obtain:

- BPD is the diameter of the bleed port corresponding to port 16 or port 17;
- h1 or h2 are the height for the bleed port extending into he cannula. This height is the length of the tubular portion of the bleed port;
- IDS is the immediate dead space volume corresponding to the sum of the volumes 40 42 and 44 and 48 and 46;
- X is the cross section area in mm squared of the volume 40 that corresponds to a portion of the plenum fed by the inducted flow from the positive air pressure supply 24;
- L is the distance between the two bleed ports shown in the preferred embodiment seen in FIG. 7 inter alia;
- F is the flow rate in ml per sec of the inducted flow into the cannula, in general one half the flow enters the right delivery tube 20 and one half enters the left delivery tube 21.

Figure 6:
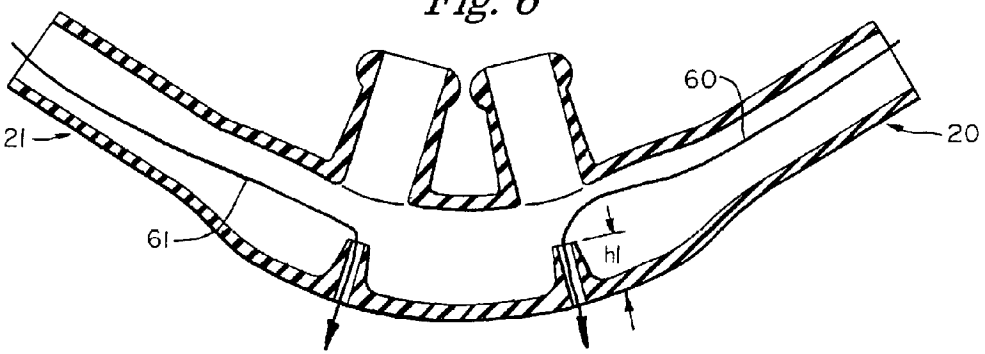
FIG. 6 is cross section of a portion of the nasal cannula showing the bleed ports; and, FIG. 7 is diagram of volumes and dimensions related to the calculation of the size and location of the bleed ports.

FIG. 6 is a composite and schematic view that shows airflow during the respiratory pause. In this phase the patient is neither inhaling or exhaling. During this portion of operation the air from the PAP ventilator 24 exits though bleed ports 16 and 17 as indicated by path arrows 60 and 61. In this figure "tall" bleed ports are depicted. The height value h1 is less than about 10 times the wall thickness at the location of the bleed port. The diameter of the bleed ports (BPD) is established to reduce the accumulation of carbon dioxide. The height of the bleed ports "h1 or h2" is established to reduce the incidence of parasitic acoustic effects. The relationship between the bleed port diameter (BPD) and the height (h1) is optimized between a value of 0.1 and 0.5. that is when 0.1=<(BPD/h1)=<0.5. It is preferred to use two bleed ports located near the inserts but other numbers and locations of bleed port are within the scope of the invention.

Example

It is now recognized that simple ventilation systems which retain a large volume of exhaled gas within the air inlet track result in increased carbon dioxide concentration in the patient's blood. An increase in dissolved carbon dioxide results in the acidification of the blood and increases respiration drive and usually increases respiration rate. In the system the dead space of the device is balanced with both the size and location of the bleed port structures to prevent build-up of the concentration of carbon dioxide in the inhaled air. When the size and location of the ports is optimized, a significant reduction in carbon dioxide gas concentration is achieved.

Generally speaking if the bleed ports are to be small, they need to be located near the nasal inserts. This effect is more important if the dead space within the cannula is large. For this reason, it should be recognized that there is a relationship between dead space, bleed port location and size which can cooperate together to provide a nasal cannula with superior performance. Although it appears that the optimized ports are restrictive due to their length and size, it has also been determined that they can be shaped to minimize parasitic acoustic effects such as "whistling" which is exhibited by current generations of current nasal cannula.

Figure 7:
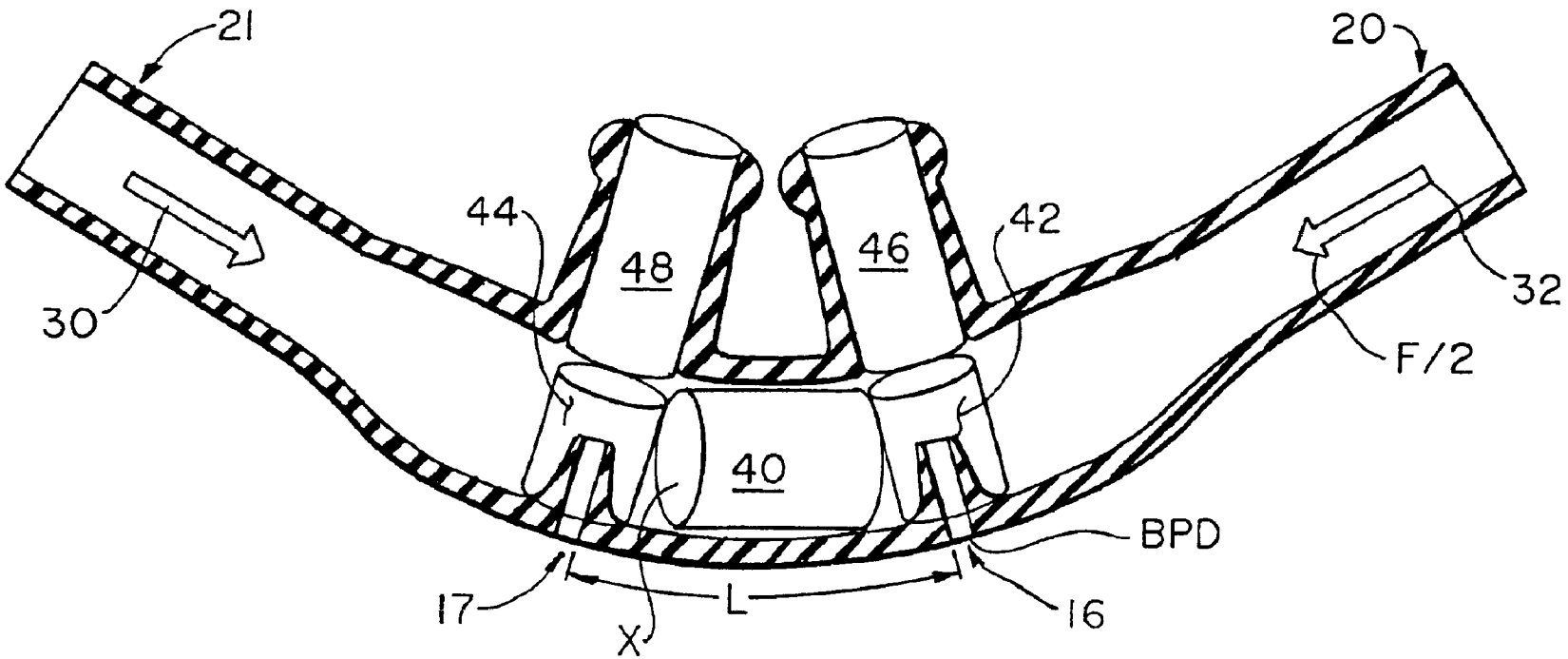

Turning to FIG. 7 the immediate dead space is the sum of all the cylinders shown in the figure as cylinders 40; 42;44; 46; and 48. The dead space is used in calculations to determine a suitable bleed port size (BPD). The immediate dead space volume is defined as the volume of the nasal inserts and the delivery tube between the inserts Simple geometry can be used to estimate the volume of the space through the cylinders depicted in FIG. 7. As the bleed ports 16 and 17 move laterally along the delivery tubes the volume of cylinder 40 increases by the distance between the inserts. Thus for the bleed port to pass the volume of the immediate dead space into the atmosphere within one second requires a computed area (BPD) related to the square root of the sum of the distance between the bleed ports. Thus for a given expiration time taken as one second and a desired concentration of carbon dioxide taken at 0.5 percent one can compute the size of the bleed port or any given distance or for any given bleed port the optimal distance between them. Based on these criteria the bleed port's diameter is related to the square root of the cross sectional area (X), the Immediate Deadspace (IDS) and the maximum system flow rate (F) as follows:

$$\text{(BPD) Bleed Port Diameter} = 2\sqrt{\frac{X * IDS}{\pi * F}}$$

A first level approximation identifies that for a given bleed port of area (BPD), the separation distance of the bleed ports is inversely related to the square of the cannula cross sectional area (X)(see FIG. 7) and directly related to the maximum system flow rate (F) as follows:

$$\text{Bleed port separation distance} \approx \frac{A*F}{X^2}$$

where "A" is the constant of proportionality for the expression and may be solved with reference to the given and established relationships.

It should be noted that if the ports are very far apart they need to be large to reach the carbon dioxide reduction goal, but such large bleed ports reduce the pressure in the system by such a large margin that it no longer effectively provides the positive pressure assistance.

Representative prototype devices have been fabricated with a diameter (to match cross sectional area X) of between ⅜ and ⅝ inches and other dimensions may be approximately scaled from FIG. 2.

Various modification and additions to the invention may be made without departing from the scope of the invention.

What is claimed is:

1. A nasal cannula for use with a constant positive pressure air supply, comprising:

first and second nasal inserts for insertion into a patient's nares;

said inserts adapted for a sealing relationship with the patient's nares;

a left and a right delivery tube, each coupled to both of said nasal inserts, each of said delivery tubes is sufficient to provide all of the air required by the patient;

a coupler located remote from said nasal inserts for coupling said cannula to a source of respiration gas;

two tubular bleed ports having an internal lumen directly opening into said delivery tubes connecting an interior of the cannula with an exterior of the cannula;

each of said bleed ports having a characteristic area expressed as a bleed port diameter called BPD, and separated by a distance called L;

each of said tubular bleed ports located beneath each of said nasal inserts such that a first bleed port is located beneath a first insert and a second bleed port is located beneath a second insert, for preferentially intercepting expired gas during exhalation;

the sum total of said bleed port diameters, called the Total Bleed Port Diameter (TBPD), have a T BPD/L ratio of between 0.1 and 0.5 such that for the two bleed ports: 0.5>2*BPD/L>0.1

2. A nasal cannula for use with a constant positive pressure air supply, supplying air (F) at between about 10 to 50 liters/minutes, said cannula comprising:

first and second nasal inserts for insertion into a patient's nares;

said inserts adapted for a sealing relationship with the patients nares;

a left and right delivery tube coupled to both of said nasal inserts, each of said delivery tubes is sufficient to provide all of the air (F) required by the user;

each nasal insert communicates with both the left delivery tube and right delivery tube;

a coupler located remote from said nasal inserts for coupling said cannula to a source of respiration air;

at least two bleed ports having an internal lumen directly opening into said delivery tubes connecting the interior of the cannula with the exterior of the cannula;

said bleed port active during exhalation to remove respired air from the cannula;

each of said bleed ports located beneath each of said nasal inserts for preferentially intercepting expired gas during exhalation;

each of said bleed ports has an individual diameter size (BPD) which is approximated by $$\text{(BPD) Bleed Port Diameter} = 2\sqrt{\frac{X*IDS}{\pi*F}}$$

where IDS is the immediate dead space volume of the delivery tubes proximate the nares, and 'X' is the cross section area of the cylinder volume of the delivery tubes between said bleed ports.

3. A nasal cannula for use with a constant positive pressure air supply for supplying air (F) between about 10 to 50 liters/minutes, said cannula comprising:

first and second nasal inserts for insertion into a patient's nares; said inserts adapted for a sealing relationship with the patients nares;

a left and right delivery tube coupled to both of said nasal inserts, each of said delivery tubes is sufficient to provide all of the air (F) required by the user, each nasal insert communicates with both the left delivery tube and right delivery tube;

a coupler located remote from said nasal inserts for coupling said cannula to a source of respiration gas;

at least two bleed ports having an internal lumen directly opening into said delivery tubes connecting the interior of the cannula with the exterior of the cannula;

said bleed port active during exhalation to remove respired air from the cannula;

each of said bleed ports located beneath each of said nasal inserts for preferentially intercepting expired gas during exhalation;

said bleed ports when two in number and they have a separation distance (L) which is approximated by;

$$\text{(L) bleed port separation distance is approximately} \approx \frac{A*F}{X^2};$$

where 'A' is a constant of proportionality an 'X' is the cross sectional area of the delivery tubes.

*4. A nasal cannula for use with a constant positive pressure air supply, comprising:*

*left and right delivery tubes, each tube having a size sufficient to provide all the air required by a patient;*

*first and second nasal inserts for insertion into a patient's nares, said inserts connected to and extending at an angle relative to respective portions of said tubes;*

*said nasal inserts each being elongated and comprising a soft, compliant material configured to conform to the cross-section of a nare of a patient when inserted into a nare up to a location where the inner cross-section of the nare equals the outer cross-section of the insert to effect said sealing relationship with the patient's nares; and*

*two tubular bleed ports, each bleed port having an open internal lumen directly opening into a respective delivery tube and connecting an interior of the delivery tube with an exterior of the delivery tube; and*

*wherein each bleed port is located directly opposite and aligned with a respective nasal insert, said bleed ports comprising together one of three air exit paths leading away from the nasal inserts.*

*5. The nasal cannula as claimed in claim 4, including a soft flange located at a distal terminal end of each nasal insert, each flange readily conformable with a patient's nare and enabling a sealing with the interior of a nare in which the insert is placed when the insert is inserted up to a location where the cross-section of the flange equals the cross-section of the nare.*

*6. The nasal cannula as claimed in claim 5, wherein said left and right delivery tubes include portions adjacent to the nasal inserts, wherein said delivery tube portions adjacent to the nasal inserts, the nasal inserts and the flanges are made in one integral piece.*

*7. The nasal cannula as claimed in claim 6, wherein said delivery tube portions adjacent the nasal inserts, the nasal inserts and the flanges are made of silicone rubber.*

*8. The nasal cannula as claimed in claim 4, further comprising a coupler located remote from said nasal inserts for enabling coupling said delivery tubes to a source of respiration gas.*

*9. The nasal cannula as claimed in claim 4, wherein each bleed port extends inwardly of an inner wall of a respective delivery tube, and comprises a bleed tube that extends toward a respective nasal insert.*

*10. The nasal cannula as claimed in claim 4, wherein said delivery tubes include portions generally aligned adjacent to the nasal inserts so as to feed pressurized air towards a central area between the delivery tubes beneath the nasal inserts, and wherein each bleed port comprises a bleed tube extending into the interior of a respective delivery tube from an inner wall thereof in a direction generally normal to the direction of motion of the air supply flowing in the respective delivery tube, each bleed tube further extending toward and parallel with a respective nasal insert.*

*11. The nasal cannula as claimed in claim 10, each bleed tube terminating at a location spaced inwardly from an inner wall of a respective delivery tube and directly opposite an inner end of a respective nasal insert at its juncture with a delivery tube.*

*12. The nasal cannula as claimed in claim 11, wherein each delivery tube has a wall thickness, and each bleed tube has a characteristic height that is at least twice and less than 10 times the wall thickness of a respective delivery tube at the location of the bleed tube.*

*13. The nasal cannula as claimed in claim 10, wherein the bleed tube has a tapered outer shape, tapering inwardly from the respective delivery tube inner wall towards each nasal insert.*

*14. The nasal cannula as claimed in claim 10, wherein the cannula, including nasal inserts, bleed tubes, and at least part of the delivery tubes adjacent to the nasal inserts, are made in a single unitary and integral piece.*

*15. The nasal cannula as claimed in claim 14, wherein the cannula, including said nasal inserts, bleed tubes and said at least part of the delivery tubes adjacent to the nasal inserts, are made of silicone rubber.*

* * * * *

UNITED STATES PATENT AND TRADEMARK OFFICE

CERTIFICATE OF CORRECTION

PATENT NO. : RE42,843 E
APPLICATION NO. : 11/334822
DATED : October 18, 2011
INVENTOR(S) : Strickland et al.

It is certified that error appears in the above-identified patent and that said Letters Patent is hereby corrected as shown below:

On the Title Page:

Item [64], Replace sub-heading, PCT Filed: with sub-heading, Filed.

Signed and Sealed this
First Day of November, 2011

David J. Kappos

David J. Kappos
*Director of the United States Patent and Trademark Office*